(12) United States Patent
Broad (10) Patent No.: US 12,239,851 B2
(45) Date of Patent: Mar. 4, 2025

(54) LEAF FOR A MULTI-LEAF COLLIMATOR

(71) Applicant: Elekta Limited, Crawley (GB)

(72) Inventor: Martin Broad, Crawley (GB)

(73) Assignee: Elekta Limited, Crawley (GB)

( * ) Notice: Subject to any disclaimer, the term of this patent is extended or adjusted under 35 U.S.C. 154(b) by 354 days.

(21) Appl. No.: 17/906,179

(22) PCT Filed: Mar. 12, 2021

(86) PCT No.: PCT/EP2021/056282
§ 371 (c)(1),
(2) Date: Sep. 12, 2022

(87) PCT Pub. No.: WO2021/180905
PCT Pub. Date: Sep. 16, 2021

(65) Prior Publication Data
US 2023/0110626 A1    Apr. 13, 2023

(30) Foreign Application Priority Data

Mar. 13, 2020 (GB) ..................... 2003679

(51) Int. Cl.
| | | |
|---|---|---|
| *A61B 6/06* | (2006.01) | |
| *A61N 5/10* | (2006.01) | |
| *G21K 1/04* | (2006.01) | |

(52) U.S. Cl.
CPC .......... *A61N 5/1045* (2013.01); *G21K 1/046* (2013.01)

(58) Field of Classification Search
CPC .......... A61B 6/06; A61N 5/10; A61N 5/1042; A61N 5/1045; G21K 1/04; G21K 1/046
See application file for complete search history.

(56) References Cited

U.S. PATENT DOCUMENTS

| | | |
|---|---|---|
| 6,459,769 B1 | 10/2002 | Cosman |
| 7,085,355 B1 | 8/2006 | Albagli et al. |
| 7,167,542 B2 | 1/2007 | Juschka et al. |
| 8,384,049 B1 | 2/2013 | Broad |
| 8,718,234 B2 | 5/2014 | Echner |
| 10,857,385 B2 | 12/2020 | Xiao et al. |
| 2002/0101959 A1 | 8/2002 | Kato et al. |
| 2006/0067480 A1 | 3/2006 | Juschka et al. |
| 2006/0193441 A1 | 8/2006 | Cadman |
| 2009/0147917 A1 | 6/2009 | Mohr |
| 2009/0262901 A1 | 10/2009 | Broad et al. |

(Continued)

FOREIGN PATENT DOCUMENTS

| | | |
|---|---|---|
| CN | 201226257 Y | 4/2009 |
| CN | 202128818 U | 2/2012 |

(Continued)

OTHER PUBLICATIONS

"International Application Serial No. PCT/EP2021/056282, International Search Report dated Jun. 16, 2021", (Jun. 16, 2021), 3 pgs.

(Continued)

*Primary Examiner* — Jurie Yun
(74) *Attorney, Agent, or Firm* — Schwegman Lundberg & Woessner, P.A.

(57) ABSTRACT

A leaf for a multi-leaf collimator comprises a leaf portion for delineating a beam of radiation, the leaf portion having first attenuation factor. The leaf also comprises a tail portion having a second attenuation factor, the first attenuation factor being greater than the second attenuation factor.

10 Claims, 5 Drawing Sheets

(56) References Cited

U.S. PATENT DOCUMENTS

| | | |
|---|---|---|
| 2011/0026683 A1 | 2/2011 | Broad et al. |
| 2011/0199085 A1 | 8/2011 | Allen et al. |
| 2012/0076269 A1 | 3/2012 | Roberts |
| 2013/0000428 A1 | 1/2013 | Ji et al. |
| 2015/0170778 A1 | 6/2015 | Echner et al. |
| 2017/0087386 A1 | 3/2017 | Mellenberg et al. |
| 2017/0128746 A1 | 5/2017 | Zwart et al. |
| 2017/0148536 A1 | 5/2017 | Kawrykow et al. |
| 2018/0012676 A1 | 1/2018 | Xu et al. |
| 2018/0035969 A1 | 2/2018 | Jin |
| 2018/0161602 A1 | 6/2018 | Kawrykow et al. |
| 2019/0001153 A1 | 1/2019 | Jones et al. |
| 2019/0054316 A1 | 2/2019 | Sheng et al. |
| 2020/0185119 A1 | 6/2020 | Stahl et al. |
| 2020/0304045 A1 | 9/2020 | Ye et al. |
| 2021/0187322 A1 | 6/2021 | Zhong et al. |
| 2021/0290979 A1 | 9/2021 | Liu et al. |
| 2023/0100438 A1 | 3/2023 | Broad |
| 2023/0101881 A1 | 3/2023 | Broad |
| 2023/0113879 A1 | 4/2023 | Broad |
| 2023/0173304 A1 | 6/2023 | Broad |

FOREIGN PATENT DOCUMENTS

| | | |
|---|---|---|
| CN | 204502129 U | 7/2015 |
| CN | 205460495 U | 8/2016 |
| CN | 205656865 U | 10/2016 |
| CN | 205843700 U | 12/2016 |
| CN | 107929955 A | 4/2018 |
| CN | 110538387 A | 12/2019 |
| DE | 3030332 A1 | 2/1982 |
| EP | 0314214 A2 | 5/1989 |
| EP | 3053628 A1 | 8/2016 |
| EP | 3266501 A1 | 1/2018 |
| GB | 2423909 | 9/2006 |
| JP | 2006081585 A | 3/2006 |
| JP | 2008206563 A | 9/2008 |
| WO | WO-2008076035 A1 | 6/2008 |

OTHER PUBLICATIONS

"International Application Serial No. PCT/EP2021/056282, Written Opinion dated Jun. 16, 2021", (Jun. 16, 2021), 5 pgs.
"United Kingdom Application Serial No. 2003679.4, Examination Report dated Sep. 15, 2020", (Sep. 15, 2020), 8 pgs.
"U.S. Appl. No. 17/906,147 Preliminary Amendment Filed with Application", 8 pgs.
"U.S. Appl. No. 17/906,149 Preliminary Amendment Filed with Application", 7 pgs.
"U.S. Appl. No. 17/906,153 Preliminary Amendment Filed with Application", 8 pgs.
"International Application Serial No. PCT/EP2021/056270, International Search Report dated Jun. 17, 2021", (Jun. 17, 2021), 3 pgs.
"International Application Serial No. PCT/EP2021/056270, Written Opinion dated Jun. 17, 2021", (Jun. 17, 2021), 5 pgs.
"International Application Serial No. PCT/EP2021/056276, International Search Report dated Jun. 17, 2021", (Jun. 17, 2021), 3 pgs.
"International Application Serial No. PCT/EP2021/056276, Written Opinion dated Jun. 17, 2021", (Jun. 17, 2021), 5 pgs.
"International Application Serial No. PCT/EP2021/056278, International Search Report dated Jun. 16, 2021", (Jun. 16, 2021), 3 pgs.
"International Application Serial No. PCT/EP2021/056278, Written Opinion dated Jun. 16, 2021", (Jun. 16, 2021), 6 pgs.
"International Application Serial No. PCT/EP2021/056281, International Search Report dated Jun. 16, 2021", (Jun. 16, 2021), 3 pgs.
"International Application Serial No. PCT/EP2021/056281, Written Opinion dated Jun. 16, 2021", (Jun. 16, 2021), 5 pgs.
"United Kingdom Application Serial No. 2003664.6, Examination Report dated Aug. 13, 2020" (Aug. 13, 2020), 7 pgs.
"United Kingdom Application Serial No. 2003673.7, Examination Report dated Sep. 15, 2020" (Sep. 15, 2020), 6 pgs.
"United Kingdom Application Serial No. 2003688.5, Examination Report dated Aug. 14, 2020" (Aug. 14, 2020), 6 pgs.
"United Kingdom Application Serial No. 2003694.3, Combined Search and Examination Report mailed Sep. 15, 2020", 7 pgs.
"U.S. Appl. No. 17/906,149, Non Final Office Action mailed Jun. 18, 2024", 12 pgs.
"U.S. Appl. No. 17/906,181, Non Final Office Action mailed Jul. 5, 2024", 9 pgs.
English Translation of JP2008206563A, (2008), cited in U.S. Appl. No. 17/906,181, Non Final Office Action mailed Jul. 5, 2024, 10 pages.
English Translation of CN202128818U, (2012), cited in U.S. Appl. No. 17/906,181, Non Final Office Action mailed Jul. 5, 2024, 3 pages.
"U.S. Appl. No. 17/906,147, Notice of Allowance mailed Jul. 12, 2024", 8 pgs.
"U.S. Appl. No. 17/906,147, Corrected Notice of Allowability mailed Aug. 1, 2024", 2 pgs.
"U.S. Appl. No. 17/906,149, Response filed Aug. 20, 2024 to Non Final Office Action mailed Jun. 18, 2024", 7 pgs.
"U.S. Appl. No. 17/906,149, Notice of Allowance mailed Sep. 6, 2024", 7 pgs.
"U.S. Appl. No. 17/906,181, Response filed Oct. 7, 2024 to Non Final Office Action mailed Jul. 5, 2024", 11 pgs.
"U.S. Appl. No. 17/906,153, Non Final Office Action mailed Oct. 16, 2024", 13 pages.
"CN-107929955 Machine Translation" (2018) from U.S. Appl. No. 17/906,153, Non Final Office Action mailed Oct. 16, 2024, 15 pages.

LEAF FOR A MULTI-LEAF COLLIMATOR

PRIORITY APPLICATIONS

This application is a U.S. National Stage Filing under 35 U.S.C. § 371 from International Application No. PCT/EP2021/056282, filed on Mar. 12, 2021, and published as WO2021/180905 on Sep. 16, 2021, which claims the benefit of priority to United Kingdom Application No. 2003679.4, filed on Mar. 13, 2020; the benefit of priority of each of which is hereby claimed herein, and which applications and publication are hereby incorporated herein by reference in their entireties.

FIELD

The present disclosure relates to a leaf for a multi-leaf collimator.

BACKGROUND

Radiotherapeutic apparatus involves the production of a beam of ionising radiation, usually x-rays or a beam of electrons or other sub-atomic particles. This is directed towards a cancerous region of a patient, and adversely affects the tumour cells causing an alleviation of the patient's symptoms. The beam is delimited so that the radiation dose is maximised in the tumour cells and minimised in healthy cells of the patient, as this improves the efficiency of treatment and reduces the side effects suffered by a patient.

In a radiotherapy apparatus, the beam can be delimited using a beam limiting device such as a 'multi-leaf collimator' (MLC). This is a collimator which consists of a large number of elongate thin leaves arranged side to side in an array. The leaves are usually made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

The leaves of the multi leaf collimator provide the important function of attenuating the radiation to protect healthy tissue surrounding target tissue. As explained above, the leaves are made from tungsten or other high-atomic-number materials. However, such material is expensive, heavy and difficult to process.

It is desirable to provide a multi-leaf collimator which addresses the abovementioned problems.

SUMMARY

Aspects and features of the present invention are set out in the accompanying claims.

To reduce the amount of tungsten (which is heavy and expensive) in the leaf, the tail portion of the leaf which is not required to attenuate the beam is either fabricated from a different material to the leaf or is thinner or narrower. Advantageously, the resultant leaf is lighter and/or cheaper and/or more easily fabricated. If the tail portion is fabricated from a different material, the tail portion can be more easily machined.

Relative Attenuation Factors

Therefore, there is provided a leaf for a multi-leaf collimator including a leaf portion for delineating a beam of radiation, the leaf portion having first attenuation factor; and a tail portion having a second attenuation factor, the first attenuation factor being greater than the second attenuation factor.

The first and second attenuation factors characterise the amount of radiation attenuation when the leaf portion and tail portion, respectively, are placed wholly in the path of the radiation beam in the orientation of intended use of the leaf. The attenuation factors are measurable at the wavelength(s) (or energies) of the radiation emitted by the radiotherapy device in which the multi-leaf collimator is configured to be installed. The range of energies in a Linac (linear accelerator-type) radiotherapy device can be 6 MeV to 25 MeV, or a subrange therein, e.g. 6 MeV to 10 MeV. The attenuation factors are those which are measurable in the direction of propagation the beam of radiation when the multi-leaf collimator is in situ in the radiotherapy device. Therefore, the attenuation factors are those measurable from a first edge of the leaf to a second edge of the leaf opposite the first edge of the leaf, the first and second edges being those lying perpendicular to the direction of propagation of the beam when the leaf is in situ in the multi leaf collimator and when the multi leaf collimator is in situ in the radiotherapy device.

The first attenuation factor is measurable by irradiating the leaf portion normal to its first edge with a uniform intensity radiation beam having the wavelength spectrum of the type used in the radiotherapy device. If leaf portion is placed so that its silhouette falls entirely within the cross section of the radiation beam, the attenuation factor can be ascertained by measuring total power attenuation of the beam due to the leaf portion. A model or calculation can take the place of the measurement. The skilled person knows how to calculate the level of attenuation based on the aforementioned conditions based on the material and dimensions of the leaf portion and the radiation beam characteristics. If the attenuation factor of the tail portion is measured or calculated in the same way using the same beam (i.e. inter alia the same power, same wavelength spectrum, same beam radius), the attenuation factors can be compared to ascertain the relative attenuation factor of the leaf portion and tail portion.

In embodiments, the first attenuation factor is greater than the second attenuation factor due to one or more of the following relative attributes of the leaf portion and tail portion.

i. The leaf portion has a greater thickness than the tail portion.
ii. The leaf portion material has a greater attenuation coefficient than the tail portion material.
iii. The leaf portion has a greater width than the tail portion.
iv. The leaf portion has a greater length than the tail portion.

A useful measure to further distinguish the characteristics of the leaf portion and the tail portion is the attenuation factor per unit length. The attenuation factor per unit length of the leaf portion can be ascertained by dividing the attenuation factor by the length of the leaf portion (the dimension in the first direction described herein from tip to tail of the leaf portion). The attenuation factor per unit length of the tail portion can be ascertained by dividing its attenuation factor by the length of the tail portion (the dimension in the first direction described herein from tip to tail of the tail portion). The lengths may be the average (i.e. mean) lengths of the leaf and tail portions.

Embodiments provide a leaf for a multi-leaf collimator including a leaf portion for delineating a beam of radiation, the leaf portion having first attenuation factor per unit length; and a tail portion having a second attenuation factor per unit length, the first attenuation factor per unit length being greater than the second attenuation factor per unit length. That is, the first attenuation factor divided by the mean length of the leaf portion is greater than the second attenuation factor divided by the mean length of the tail portion.

Another useful measure to distinguish the characteristics of the leaf portion and the tail portion is the attenuation factor per unit width. The attenuation factor per unit width of the leaf portion can be ascertained by dividing the attenuation factor by the width of the leaf portion (the dimension in the fourth direction described herein from the first edge to the second edge of the leaf portion, i.e. in the dimension parallel to the direction of propagation of the radiation beam). The attenuation factor per unit width of the tail portion can be ascertained by dividing its attenuation factor by the width of the tail portion (the dimension in the fourth direction described herein from the first edge to the second edge of the tail portion). The above described widths may be the average (i.e. mean) widths of the leaf and tail portions.

Embodiments provide a leaf for a multi-leaf collimator including a leaf portion for delineating a beam of radiation, the leaf portion having first attenuation factor per unit width; and a tail portion having a second attenuation factor per unit width, the first attenuation factor per unit width being greater than the second attenuation factor per unit width. That is, the first attenuation factor divided by the mean width of the leaf portion is greater than the second attenuation factor divided by the mean width of the tail portion.

A yet further useful measure to distinguish the characteristics of the leaf portion and the tail portion is the attenuation factor per unit area of the face of the leaf. The reason this metric is useful is that it provides a comparison of the relative attenuating properties of the leaf portion and tail portion which is independent of both the relative mean length and relative mean width of the tail portion.

The attenuation factor per unit area of the leaf portion can be ascertained by dividing the attenuation factor by the area of the face (i.e. one face) of the leaf portion. The area of the face of the leaf may be the average (i.e. mean) width of the leaf portion (the dimension in the fourth direction described herein from the first edge to the second edge of the leaf portion) multiplied by the average (i.e. mean) length of the leaf portion (the dimension in the first direction described herein from tip to tail of the leaf portion). However, other means for ascertaining the area of the face may be more accurate and therefore more appropriate. The attenuation factor per unit area of the tail portion can be ascertained by dividing its attenuation factor by the area of the face of the tail portion.

Therefore, there is provided a leaf for a multi-leaf collimator including a leaf portion for delineating a beam of radiation, the leaf portion having first attenuation factor per unit area; and a tail portion having a second attenuation factor per unit area, the first attenuation factor per unit area being greater than the second attenuation factor per unit area.

Relative Linear Attenuation Coefficient

In some embodiments, the leaf portion has a greater attenuation factor per unit length (or per unit width or per unit area) because the leaf portion material has a greater linear attenuation coefficient than the tail portion material. In some embodiments, the leaf portion material has a higher atomic number than the tail portion material. For example, the first material may be Tungsten and the second material may be steel.

The linear attenuation coefficient describes the fraction of the radiation beam that is absorbed or scattered per unit thickness of the material. The linear attenuation coefficient is given by Equation 1.

$$\mu = -x^{-1} \ln\left(\frac{I}{I_0}\right) \qquad (1)$$

Where: I is the intensity of radiation transmitted across a distance x, $I_0$ is the initial intensity of the radiation, and $\mu$ is the linear attenuation coefficient.

The linear attenuation coefficients of some common materials at radiotherapy wavelengths can be found in the literature. However, the mass attenuation coefficient, which is density independent, is more readily available. Tables and graphs of the mass attenuation coefficients for all of the elements Z=1 to 92, and for compounds and mixtures of radiological interest are available at the National Institute for Standards and Technology website (https://www.nist.gov/pml/x-ray-mass-attenuation-coefficients). The tables on the NIST website cover energies of photons (x-ray, gamma ray, bremsstrahlung) from 1 keV to 20 MeV.

The mass attenuation coefficient can easily be converted to a linear attenuation coefficient, by multiplying it by the density of the material. That is, the linear attenuation coefficient (u), mass attenuation coefficient (M) and density ($\rho$) are related by Equation 2:

$$\mu = M\rho \qquad (2)$$

Thus, the skilled person can ascertain whether or not the leaf portion material has a greater linear attenuation coefficient than that of the tail portion material by accessing published linear attenuation coefficient data or accessing published mass attenuation coefficient data and ascertaining (by measurement or reference) the material density.

The skilled person can also can readily ascertain the linear attenuation coefficient of the leaf portion material or tail portion material through routine testing procedures. The linear attenuation coefficient of a material is the number of e-foldings of the intensity that will be had as radiation energy passes through the material per unit depth of the material. This can be ascertained by a simple measurement of the intensity attenuation of a radiation beam by a block of the material, the radiation beam having the same properties as the beam emitted by the radiotherapy device for which the leaf is intended. The linear attenuation coefficient can then be calculated using Equation 1, using the thickness of the block x.

Thus, access to known mass attenuation coefficients and/or the ability to readily measure linear attenuation coefficients allows the skilled person to select appropriate materials for the leaf portion and tail portion and/or assess whether or not the leaf portion material has a greater attenuation coefficient than the tail portion material.

The purpose of the leaf portion is to delineate the radiation beam by heavily attenuating portions of it. Therefore, the material choice is limited to high atomic number materials, such as Tungsten.

The tail portion is not used to delineate the radiation beam. Its purpose is to push and pull the leaf portion and/or to accommodate other components which drive the leaf portion in its linear trajectories into and out of the path of the radiation beam.

The inventors have recognised that the material constraints for the tail portion can therefore be relaxed in comparison with those of the leaf portion due to the difference in function of the leaf portion and tail portion. The linear attenuation coefficient of the tail portion can be lower than that of the leaf portion because the tail portion does not need to function as a beam attenuator.

Although Tungsten is the preferred material for the leaf portion, it is not essential that the leaf portion material is Tungsten. The leaf portion material can be any material suitable for attenuating radiation from a radiotherapy device to an acceptable degree, namely a degree sufficient to reduce or prevent radiation damage to healthy tissue surrounding a target tissue. The second material is also not limited to the material in the above example. For example, the second material may include copper, aluminium, nickel, titanium or an alloy containing one or more of these materials or other suitable materials.

Relative Thickness

The leaf portion thickness is governed by the multi leaf collimator design including the size of the aperture between leaf banks and the required spatial aperture resolution among other considerations. The spacing between leaf portions of adjacent leaves must be minimal to prevent radiation leakage between the leaves and recesses in the thickness of the leaf portion are undesirable due to the need for the leaf portions to uniformly attenuate the radiation beam. However, the inventors have recognised that no such constraint on the thickness needs to be applied to the tail portion, because the tail portion does not perform the function of attenuating the beam.

Thus, in some embodiments, the leaf portion has a greater attenuation factor per unit length (or per unit width or per unit area) because it has a greater thickness (dimension between the faces in the fifth direction described herein) than that of the tail portion. The thickness may be a mean thickness or a minimum thickness.

Advantageously, if the thickness of the tail portion is less than the thickness of the leaf portion, the weight of the leaf is reduced.

Further advantageously, a comparatively lower thickness in a whole or a part of the tail portion allows more room for accommodating other components in the vicinity of the tail portion. For example, a reduced thickness in part or whole of the tail portion may allow more room for accommodating a leaf drive component (such as a leaf nut or leaf nut holder) associated therewith so that it does not impinge, or does not impinge too far, into the space adjacent the tail portion. This, in turn, reduces interference between adjacent leaves and their associated leaf drive components, or allows more freedom in design to mitigate interference, than if the tail portion and leaf portion thicknesses are identical to each other.

Relative Width

The leaf portion width determines the amount of material between the radiation source and the healthy tissue in the treated subject. The leaf portion width is therefore governed by the attenuation requirements of the multi leaf collimator.

The width of the leaf portions must be sufficient to reduce the radiation intensity to an acceptable level. However, the inventors have recognised that no such constraint on the width needs to be applied to the tail portion, because the tail portion does not perform the function of attenuating the beam.

Thus, in some embodiments, the leaf portion has a greater attenuation factor per unit length because it has a greater width (dimension between the first and second edges in the fourth direction described herein) than that of the tail portion. The width may be a mean width or a minimum width.

Advantageously, if the width of the tail portion is less than the width of the leaf portion the weight of the leaf is reduced.

Further advantageously, a reduced width in a whole or a part of the tail portion allows more room for accommodating other components in the vicinity of the tail portion. This, in turn, reduces interference between adjacent leaves and their associated leaf drive components, or allows more freedom in design to mitigate interference, than if the tail portion and leaf portion widths are identical to each other.

Relative Ductility

Tungsten is difficult to machine owing to its very low ductility. The inventors have recognised that the difference in function between the leaf portion and tail portions means that the material constraints can be relaxed in the tail portion and this allows another material other than Tungsten to be used.

Thus, in some embodiments, the tail portion material is more ductile than the leaf portion material.

Advantageously, the tail portion has greater machinability than the leaf portion. Thus, the overall thickness of the tail portion can be controlled more easily during manufacture if a more ductile material is used. Accordingly, the cost and/or complexity of manufacture is reduced. In addition, the reduced ductility allows features to be machined into the tail portion with greater ease and at lower cost than if the tail portion is made from the same material as the leaf portion.

Recessed Parts in Tail Portion

In embodiments, the tail portion includes a recessed portion for receiving at least a part of a leaf actuator component. In some embodiments, the recessed portion is recessed from a face of the tail portion. In some embodiments, the tail portion includes a recessed portion having one or more of the following features: a slot for receiving a leaf actuator screw; a slot for receiving a leaf nut; a seat for receiving a leaf nut holder; a groove for receiving a leaf nut or leaf nut holder corresponding to an adjacent leaf.

Joining of the Leaf Portion and Tail Portion

The leaf portion and tail portion are each plate like in form and together they form a contiguous plate-like structure.

In some embodiments, the tail portion and the leaf portion are monolithic. For example, the whole leaf may be made from a single material (e.g. tungsten), but with a reduced thickness or reduced with in the tail portion.

In other embodiments, the tail portion is a separate piece of material which is coupled to the leaf portion. In this respect, the leaf portion and tail portion can be said to be modular.

In some embodiments, the leaf portion is separable from the tail portion. Advantageously, this allows replacement of the leaf portion or tail portion independently of each other. For example, if the tail portion is more ductile than the leaf portion, the tail portion may wear faster than the leaf portion. The cost of replacement of a worn tail portion is less than the cost of replacement of the whole leaf.

The coupling between the leaf portion and tail portion may be by adhesion or by fixing means, such as screws. In some embodiments, the coupling is via a joint between overlapping portions of the leaf portion and tail portion, for example via a lap joint or tongue-in-groove joint between the leaf portion and tail portion. Advantageously, this provides a strong and reliable bond between the leaf portion and tail portion which can withstand repeated shear stresses from the actuation of the leaf in its linear motion into and out of the path of the radiation beam.

Embodiments include a leaf bank including leaves having any of the structures defined herein.

Embodiments also include a multi leaf collimator having said leaf bank and/or a radiotherapy device having said multi leaf collimator.

BRIEF DESCRIPTION OF THE DRAWINGS

Specific embodiments are described below by way of example only and with reference to the accompanying drawings in which:

FIG. 3a shows a close up isometric view of the edge of the tail portion of a leaf according to an embodiment;

FIG. 3b shows a cross section of the tail portion of the leaf shown in FIG. 3a;

DETAILED DESCRIPTION OF THE DRAWINGS

MLC Assembly
Defining a Useful Co-Ordinates Convention

For ease of description, a cartesian co-ordinates system is defined in the Figures by a first direction (+y); a second direction (−y) opposite to the first direction; a third direction (+z) perpendicular to the first direction; a fourth direction (−z) opposite to the third direction; a fifth direction (+x) perpendicular to both the first direction and the third direction; a sixth direction (−x) opposite to the fifth direction. The first and third directions define a first plane (yz), the first and fifth directions define a second plane (xy) perpendicular to the first plane, and the third and fifth directions define a third plane (xz) perpendicular to the first and second planes. This co-ordinates system and convention is used consistently throughout the Figures.

Figure 1:
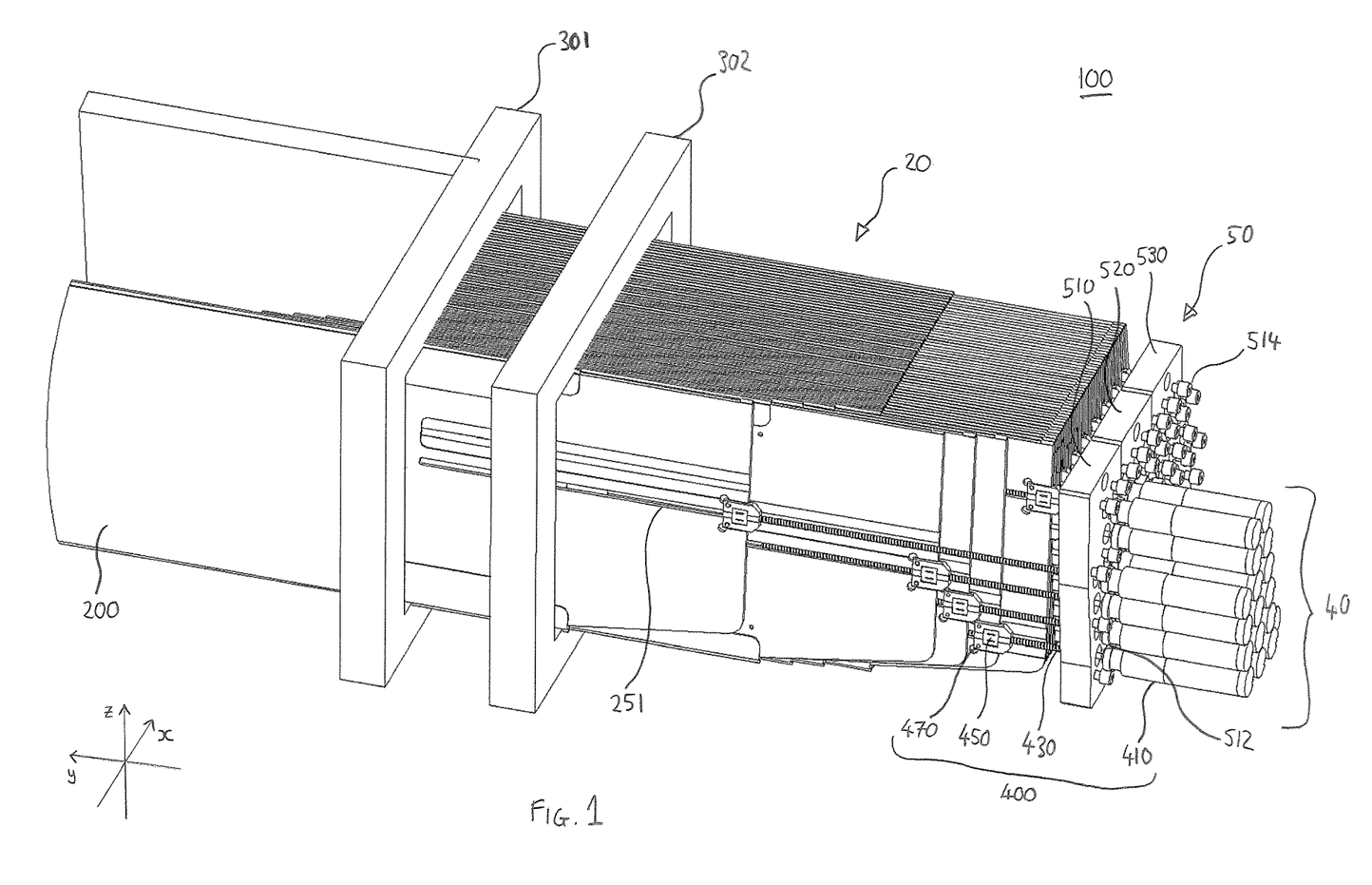
FIG. 1 shows a partially assembled multi leaf collimator.

FIG. 1 shows a partially assembled multi-leaf collimator 100 comprising a leaf bank 20, a first and second leaf guide 301, 302, a leaf drive array 40 and a leaf drive mount 50.

The leaf bank 20 includes an array of leaves 200 arranged side by side so that a face of one leaf is in contact with a face of an adjacent leaf. The leaves 200 are arranged substantially parallel to each other but a gradient in thickness in the first direction from a first edge of each leaf 200 to a second edge opposite the first edge causes the leaf bank 20 to adopt a trapezoidal cross section in the third plane as shown in FIG. 9. Thus, the plane of a leaf 200 positioned in the middle of the leaf bank 20 is arranged to be substantially parallel to the first plane (yz), but the planes of the other leaves either side of that leaf 200 form a progressively greater angle with the first plane (yz) with distance in the fifth and sixth directions from the centre of the leaf bank 20. The leaves 200 are arranged to move relative to each other in the first and second directions. The leaves 200 are described in more detail below.

The leaf drive array 40 includes a plurality of leaf drive units 400. Each leaf drive unit 400 includes a leaf motor 410, a leaf actuator screw 430, a leaf nut 450 and a leaf nut holder 470. The leaf actuator screw 430 is coupled to the leaf motor 410 and is arranged so that its axis is parallel to the first direction. The leaf motor 410 is arranged to rotate the leaf actuator screw 430 about its axis (i.e. clockwise and anti-clockwise around the first direction). The leaf nut 450 is held in position in a leaf actuator screw slot 250 in the leaf 200 by a leaf nut holder 470 fixed to the leaf 200. The leaf nut 450 is held by the leaf nut holder 470 to be static relative to the leaf 200, with the exception that a small amount of relative linear motion between the leaf nut 450 and the leaf 200 is allowed in the third and fourth directions. The leaf nut 450 contains features which interact with the leaf 200 to keep the leaf nut 450 rotationally static relative to the leaf 200. The leaf nut 450 is arranged to receive the leaf actuator screw 430 and to guide it into the leaf actuator screw slot 250. The rotational motion of the leaf actuator screw 430 translates into linear motion of the leaf nut 450, and hence the leaf 200, relative to the leaf actuator screw 430.

The leaf drive units 400 are staggered in the first direction so that the leaf nut holder 470 of any one leaf does not interfere with the leaf nut holders 470 of the leaves 200 immediately adjacent to it on either side. The leaves 200 also contain grooves to accommodate the portions of the leaf nut holders 470 of adjacent leaves 200 which are proud from the face of the leaf 200. The leaf motor 410, leaf nut 450, leaf nut holder 470 and the grooves in the leaves are described in more detail below.

The leaf drive mount 50 includes three separate mounting plates 510, 520, 530 arranged in a plane parallel to the third plane (xz). The leaf drive mount includes mounting holes 512 therein for receiving the leaf motors 410 and mounting screws 514 for securing the leaf motors 410 to the mounting plates 510, 520, 530. The leaf drive mount 50 and each of its components are described in more detail below.

The first and second leaf guide 301, 302 each comprise a rectangular frame for guiding and supporting the leaves 200 in their linear motion in the first and second directions respectively into and out of the path of the radiation beam.

A complete multi leaf collimator assembly further includes a second, opposing arrangement including leaf bank, leaf guides, leaf drive array and leaf drive mount which are arranged to substantially mirror the assembly described above relative to a plane parallel to the third plane (xz) and aligned with the centre of the axis of the radiation beam.

In use, the leaf drive arrays drive the leaves 200 of their respective leaf banks 200 to move into and out of the path of a radiation beam passing in the fourth direction through an aperture formed between the leading edges of the leaves 200 of one leaf bank 20 and those of the leaves 200 of the opposing leaf bank 20. The leaves 200 of each leaf bank 20 are moveable independently of each other, which enables the shape of the aperture to be changed according to treatment requirements. The aperture acts as a beam shaper by blocking portions the radiation beam to redefine its cross-sectional shape in the second plane (yz). That is, the radiation beam having passed through the aperture takes on the cross-sectional shape of the aperture in the second plane (yz).

Composite Leaf

The leaf 200 can be formed from a monolithic plate comprising a single material. Alternatively, the leaf 200 can be a composite leaf comprising two plates of different materials joined together such that the plates are coplanar.

Introduction to Leaf Portion and Tail Portion

Figure 2A:
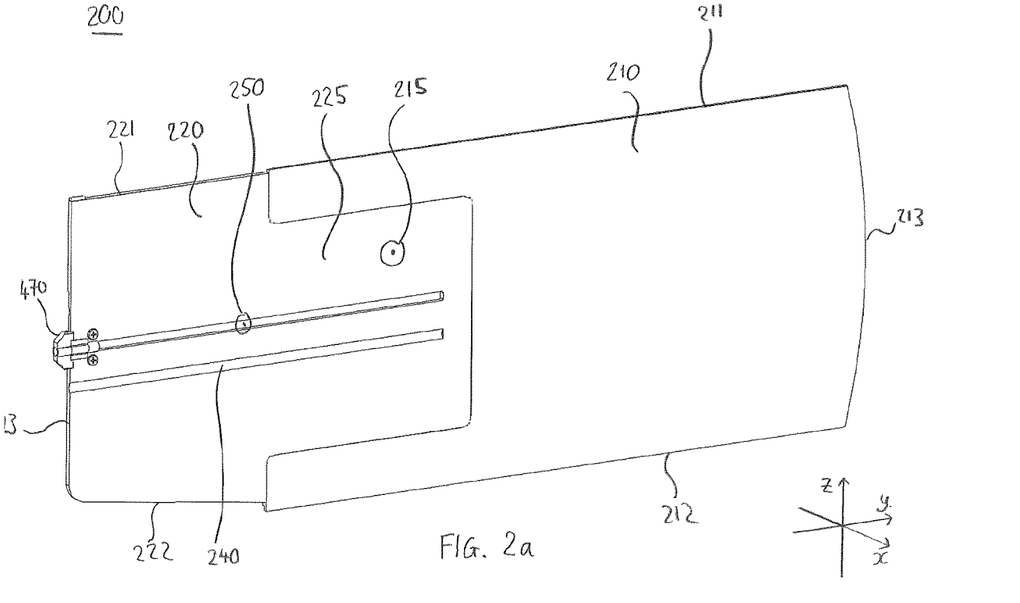
FIGS. 2a and 2b show isometric views of a leaf according to an embodiment.
Figure 2B:
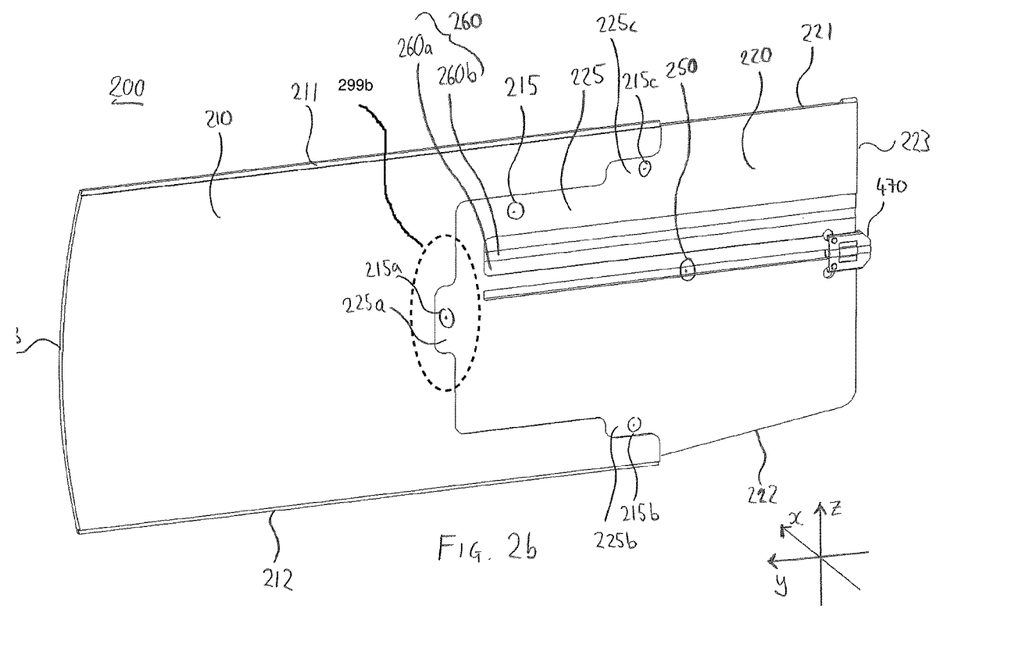

FIGS. 2a and 2b each show a different isometric view of such a composite leaf 200. The composite leaf includes a leaf portion 210 and a tail portion 220. The composite leaf 200 is formed as a flat, substantially rectangular-shaped plate, notwithstanding the shape of some of the edges of the composite leaf 200 described below. The leaf portion 210 and the tail portion 220 form a first and second area of the plate, respectively. The average thickness of the composite leaf 200 is small relative to its width and length. The central plane of the tail portion 220 is coplanar with that of the leaf portion 210.

The leaf portion 210 is made from a high atomic numbered material, e.g. tungsten, so that it is substantially opaque to the radiation. The purpose of the leaf portion 210 is to block a portion of the radiation beam. The leaf portions 210 of all leaves 200 in the leaf bank 20 act together to form the edge of the aperture for shaping the radiation beam. In contrast, the tail portion 220 plays no part in attenuating or blocking parts of the radiation beam. The tail portion 220 operates to push and pull the leaf portion 210 into and out of the path of the radiation beam. Thus, functionally, the tail portion can be thought of as part of (e.g. an extension of) the leaf drive mechanism. As such, the tail portion does not need to be made of a high atomic number material and can be made from a thinner plate than the leaf portion. Furthermore, the tail portion can be manufactured from a material which is lighter and/or easier to machine than tungsten. Greater ease of machining allows functional features to be added to the tail portion 220 (e.g. the features described below) which would be much more difficult, time intensive or cost intensive to machine into the high atomic numbered material of the leaf portion 210.

Relative Alignment of the Composite Leaf in the Co-Ordinates System

The plane of the composite leaf 200 is in the first plane (yz) when in situ in the multi leaf collimator, with the long edges and short edges of the rectangular shape of the composite leaf 200 being aligned in the first and third directions, respectively. The composite leaf 200, and therefore the tail portion 220 and the leaf portion 210, each have a first face and a second face on the opposite side to the first face, and both faces lie substantially parallel to the first plane (yz). FIG. 2a shows an isometric view from one side of the leaf 200 including the first face and FIG. 2b shows an isometric view from the other side of the leaf 200 including the second face.

Shapes of the Leaf Portion and Tail Portion

The first area comprises a first substantially rectangular area having a U-shaped recess 215 recessed from one side thereof, the recess 215 extending in the first direction into the first substantially rectangular area. The second area comprises a second substantially rectangular area defining a main body of the tail portion 220 and a tongue 225 protruding in the first direction from one edge of the main body. The tongue 225 has a shape and dimensions which correspond to those of the recess 215 of the first area. The tongue 225 is received in the recess 215 when the leaf portion 210 and the tail portion 220 are joined. The substantially rectangular shape of the composite leaf 200 is formed by the outline of the composite shape defined by the first area and second area.

The leaf portion 210 has a first edge 211 aligned with the first direction, a second edge 212 opposite the first edge 211 and aligned with the first direction, and a third edge 213 opposite the recess 215 and aligned with the third direction. The first edge 211 is part of the top edge of the composite leaf 200 when the leaf 200 is in situ in the multi-leaf collimator 100 and the radiation beam is directed vertically downward (i.e. in the fourth direction). The third edge 213 opposite the recess 215 is the leading edge of the leaf portion 210 and is the part of the leaf portion 210 which is closest to the axis of the radiation beam in use. The leading edge is slightly convex in the third direction (i.e. curved outwardly from the main part of the leaf portion 210 in the first plane) and has a radius of curvature which is greater than the length of the leaf 200 in the first direction.

The tail portion 220 has a first edge 221 aligned with the first direction, a second edge 222 opposite the first edge and oblique to the first direction and a third edge 223 opposite the tongue 225 and aligned with the third direction. The third edge 223 is the trailing edge of the composite leaf 200, meaning it is the furthest edge from the axis of the radiation beam in use. The first edge is part of the top edge of the composite leaf 200 when the leaf 200 is in situ in the multi-leaf collimator 100 in use when the radiation beam is directed vertically downward.

Recess in Tail Portion for Allowing Clearance for a Leaf Drive Component

The leaf drive components for driving an individual leaf may include the leaf nut, leaf nut holder and leaf actuator screw. The thickness (i.e. dimension in the direction normal to the plane of the leaf) or diameter of the leaf drive components affects both their suitability to fit in the confined spaces behind the leaves and their stability in operation. In general, the greater the thickness or diameter, the more stable the leaf drive component is in operation but the more difficult it is to accommodate multiple leaf drive components in close proximity to each other and the leaves. Thus, there is a trade-off between the size of the leaf drive components and their stability.

In general terms, the present disclosure provides a leaf for a multi-leaf collimator, the leaf comprising a leaf portion and a tail portion, the tail portion including a longitudinally extending recess for accommodating (or receiving) at least a portion of a leaf drive component. The leaf drive component is associated with (that is, it may be arranged to drive) the leaf itself or an adjacent leaf. This may prevent the leaf drive component from interfering with the motion of the leaf itself or interfering with the motion of an adjacent leaf and/or adjacent leaf drive component. The thickness or diameter of the leaf drive component can therefore be greater than the thickness of the individual leaves (or the pitch between adjacent leaves where there is a clearance between the leaves). Larger leaf drive components can improve the stability of the leaf drive mechanism and hence the maximum speed of the leaves can be increased.

The leaf is for use in a multi-leaf collimator having a plurality of leaves and a plurality of leaf drive components, wherein each leaf drive component is configured to drive a respective leaf.

There is also provided in a multi-leaf collimator having a plurality of leaves and a plurality of leaf drive components, wherein each leaf drive component is configured to drive a respective leaf. At least one of the leaves comprises a leaf portion and a tail portion, the tail portion including a longitudinally extending recess for accommodating a leaf drive component associated with the leaf itself or an adjacent leaf. In embodiments, the leaf drive components are identical so that the longitudinally extending recess is identical in form in each leaf. The leaf drive components may be staggered in the vertical (z) direction. In this case, if the longitudinally extending recess is arranged to accommodate a leaf drive component of an adjacent leaf, the position of the longitudinally extending recess in each leaf will also be staggered in the vertical (z) direction. Thus, the longitudinally extending recesses may be identical in form but differ in its position on or in the leaf depending on the position of the leaf within the leaf bank.

Several examples of a longitudinally extending recess are described below with reference to FIGS. 2a, 2b, 3a, 3b, 4a and 4b.

Leaf Actuator Screw Slot 250

The tail portion 220 has a through slot therein extending in the first direction, the through slot may be described as a leaf actuator screw slot 250. The leaf actuator screw slot 250 extends from the third edge 223 of the tail portion 220 towards a terminal end of the tongue 225. The leaf actuator screw slot 250 extends in both the main body of the tail portion 220 and the tongue 225 and terminates before the end of the tongue 225.

Figures 3A, 3B:
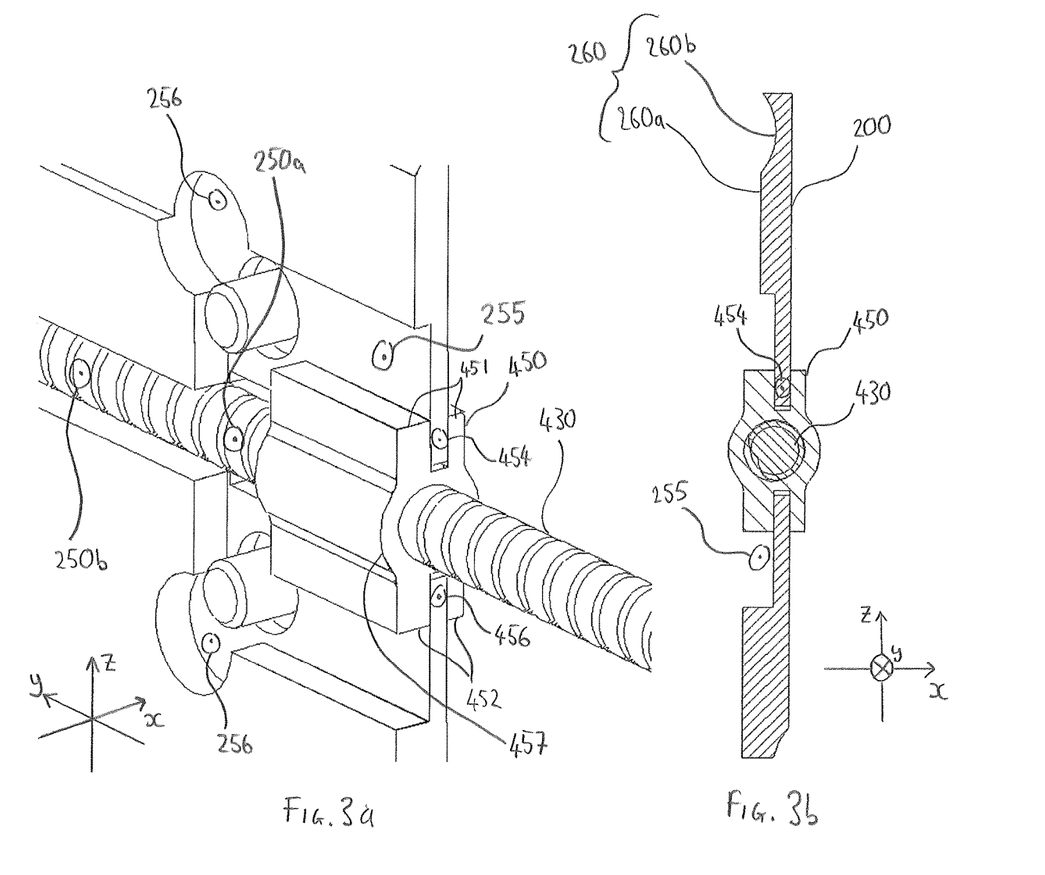

As shown in FIG. 3a, which is described in more detail below, the leaf actuator screw slot 250 includes a first slot section 250a proximal to the third edge 223 and a second slot section 250b distal from the third edge 223. The second slot section 250b is immediately adjacent and contiguous with the first slot section 250a. The first slot section 250a has a width in the third direction fractionally larger than that of the second slot section 250b. The second slot section 250b is several times longer in the first direction than the first slot section 250a.

In embodiments, a slot in the leaf (e.g. the leaf actuator screw slot 250 described above) is arranged to provide clearance to accommodate misalignments between the leaf and the leaf actuator screw. That is, the slot is wider than the diameter of the leaf actuator screw so that the leave actuator screw can move up and down (i.e. in the plane of the leaf) within the slot. In other words, the slot for receiving the leaf actuator screw provides a clearance either side of the leaf actuator screw in the plane of the leaf.

The clearance may be matched to the permitted movement of the leaf nut in the third direction and fourth direction (+/−z) in the plane of the leaf (as described herein) so that the resulting position of the leaf actuator screw upon movement of the leaf nut between its extremities in the third direction and fourth direction (+/−z) is accommodated by the clearance provided by the slot. This can allow a greater range of movement of the leaf nut and leaf actuator screw relative to the leaf. Therefore, misalignments between the leaf drive components and the leaf resulting from misalignments between the leaf motor and the leaf can be accommodated to a greater degree. This can improve the stability of the leaf drive mechanism and prevent wear on the leaf nut, the leaf actuator screw and the leaf motor, thus prolonging the service life of these components.

First Groove

A first groove 240 extends from the third edge 223 of the tail portion 220 toward a terminal end of the tongue 225. The first groove 240 is located along the first face of the tail portion 220 parallel to the leaf actuator screw slot 250. The first groove 240 is offset from the leaf actuator screw slot 250 in the fourth direction. The first groove 240 and the leaf actuator screw slot 250 are substantially the same length. The first groove 240 has a cross-sectional shape the third plane (xz) of a minor segment of a circle to accommodate convex parts of the leaf nut 450 and leaf nut holder 470 which are proud from the face of an adjacent leaf 200. The composite groove 260 is shown in closer detail in FIG. 4b.

Seat

FIG. 2b shows an isometric view of the second face of the composite leaf 200. FIG. 3a shows a close up isometric view of the second face of the tail portion 220 in the region of the first slot section 250a.

The leaf actuator screw slot 250 is a through slot in that it passes through the whole thickness of the tail portion 220 from the first face to the second face. The first slot section 250a lies in the centre of a seat 255 recessed into the second face of the tail portion 220. The seat 255 has a cross section in the shape of a high-aspect-ratio (third direction length: fifth direction width) rectangle in both the second plane (xy) and the third plane (xz). The length of the seat 255 in the first direction is equal to the length of the first slot section 250a. The width of the seat 255 in the third direction is approximately equal to its length.

Through Holes, Blind Holes and Curved Rib

Two blind holes 256 are formed in the second face of the tail portion 220, the blind holes 256 being centred on corners of the seat 255 distal from the third edge 223 of the tail portion 220. The blind holes 256 have the same depth as the seat 255 so that the void defined by the seat 255 is contiguous with the blind holes 256.

Two through holes are formed through the tail portion 220, the through holes emerging in different quadrants of the seat 255 in the distal half of the seat 255 from the third edge 223 of the tail portion 220.

The tail portion 220 also includes a curved rib (shown in FIG. 4b described below) convex to the first face of the tail portion 220, the curved rib straddling the first slot section 250a between the two through holes.

Composite Groove

The second face of the tail portion 220 includes a composite groove 260 for receiving the parts of the leaf nut 450 and leaf nut holder 470 which are proud from the face of an adjacent leaf. The composite leaf 260 includes a second groove 260a and a third groove 260b of narrower width than the second groove 260a. The third groove 260b is seated inside (i.e. formed in the bottom surface of) the second groove 260a. Both the second groove 260a and the third groove 260b extend from the third edge 223 of the tail portion 220 towards a terminal end of the tongue 225. Both the second groove 260a and third groove 260b lie parallel to the leaf actuator screw slot 250 along the second face of the tail portion 220. The central axis of both the second groove 260a and third groove 260b are collinear and offset from the leaf actuator screw slot 250 in the fourth direction. The second groove 260a and third groove 260b are substantially the same length as the leaf actuator screw slot 250. The second groove 260a has the cross-sectional shape in the third plane (xz) of a high-aspect-ratio rectangle (third direction length:fifth direction width). The third groove 260b has the cross-sectional shape in the third plane (xz) of a minor segment of a circle. The cross-sectional shape of the composite groove 260 is shown in closer detail in FIG. 4a.

Figure 4A:
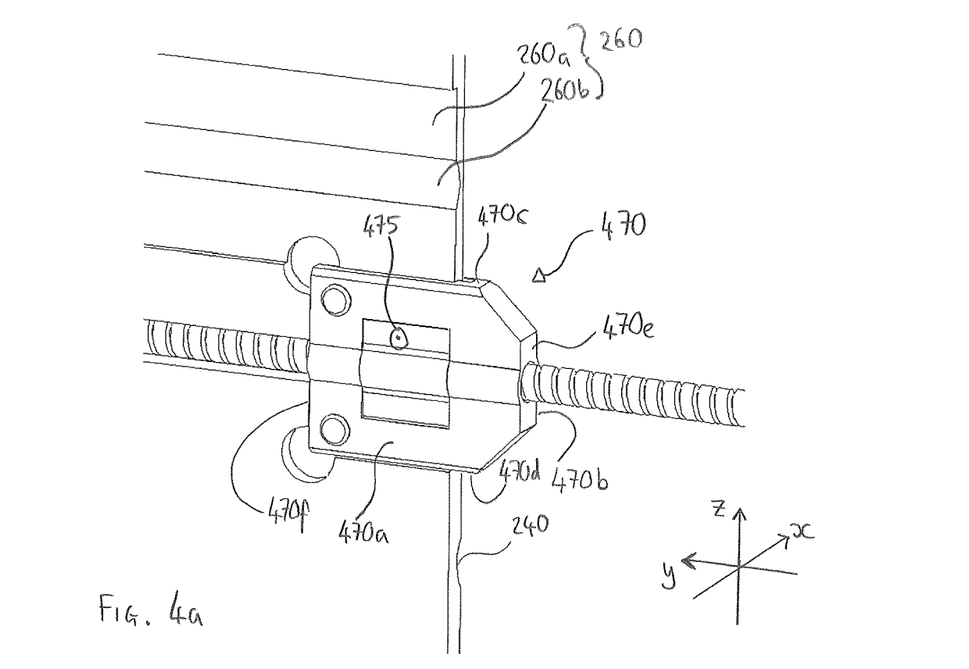
FIG. 4a shows an isometric view of a face of the tail portion of a leaf according to an embodiment.

The edge of the seat 255 closest to the first edge of the tail portion 220 is aligned with the edge of the second groove 260a so that the void defined by the seat 255 is contiguous with the void defined by the second groove 260a.

Locking Joint Between the Tail Portion and Leaf Portion

The tail portion and leaf portion can be joined via one or more lap joints as shown in FIG. 2b and described in more detail below. This requires an adhesive in the joint region and/or another fastener to prevent the tail portion from being pulled apart from the leaf portion under the forces exerted on the leaf by the leaf drive mechanism. The reliance on an adhesive for strength in the plane of the leaf can be less than ideal, because application of a suitable adhesive to create a sufficiently strong and reliable joint can complicate the fabrication process, leading to increase in the cost of manufacture.

In embodiments, the joint between the tail portion and leaf portion is configured so as to prevent the leaf portion and tail portion from being pulled apart in the direction of movement of the leaf without an adhesive. This is achieved by using a locking (or interlocking) joint between the tail portion and leaf portion. Depending on the configuration of the locking joint, an adhesive may still be required to prevent forces acting out of the plane of the leaf from separating the tail portion from the leaf portion. However, in normal operation of the MLC, the greatest force acting on the leaf usually acts in the direction of movement of the leaf (i.e. in the longitudinal direction of the leaf). The locking joint ensures that a greater proportion of the forces acting in the longitudinal direction are exerted through the leaf material than through an adhesive.

The locking joint may additionally be configured to prevent separation of the tail portion from the leaf portion due to forces acting in the plane of the leaf other than in the longitudinal direction of the leaf. For example, the locking joint may additionally mechanically prevent movement of the tail portion relative to the leaf portion in the transverse direction in the plane of the leaf (i.e. in the plane of the leaf perpendicular to the direction of travel of the leaf). The locking joint may additionally be configured to prevent relative rotational movement of the tail portion and leaf portion in the plane of the leaf.

It may be understood that the tail portion is monolithic, and the leaf portion is also monolithic. The locking joint is formed from a protrusion which is monolithic with one of the tail portion and leaf portion (whichever has the protrusion) and a corresponding recess in the other of the tail portion and leaf portion.

In addition to providing a stronger mechanical joint between the tail portion and the leaf portion, the locking joint can also ensure better alignment between the tail portion and leaf portion during manufacture and during operation of the MLC. Prevention of misalignment can ensure smoother operation of the MLC and allows tighter tolerances between the leaves and other parts of the MLC, such as the leaf guides, which in turn allows more accurate positioning of the leaves during operation of the MLC.

Examples of a locking joint are shown in FIGS. 2c-2f. Each of FIGS. 2c-2f show a close up view of a locking joint between a leaf portion and tail portion of a leaf. The leaf may be identical to those shown in FIGS. 2a and 2b, however the skilled person will appreciate that the present disclosure is not limited thereto. For example, the leaf can be a simple rectilinear shape with no other features other than the locking joint between the tail portion and leaf portion.

The position of the locking joint is generally in the central region of the leaf, for example as shown by the joint 299b in FIG. 2b. However, the locking joint position is not limited thereto and can be further toward any of the four edges of the leaf depending on the configuration (e.g. shape and/or size) of the leaf portion and tail portion.

Figure 2C:
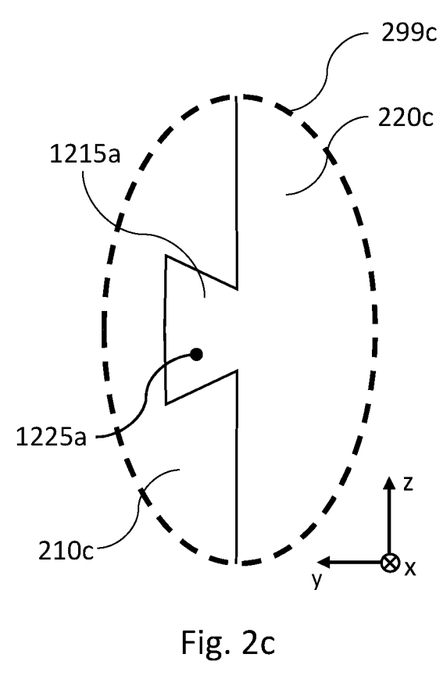
FIGS. 2c, 2d, 2e and 2f each show a close-up view of locking joint between a tail portion and leaf portion of a leaf according to an embodiment.

FIG. 2c shows a locking joint 299c including a dovetail-shaped protrusion 1215a of a tail portion 220c received by a corresponding dovetail-shaped recess 1225a in a leaf portion 210c thus forming a dovetail joint between the leaf portion 210c and tail portion 220c.

Figure 2D:
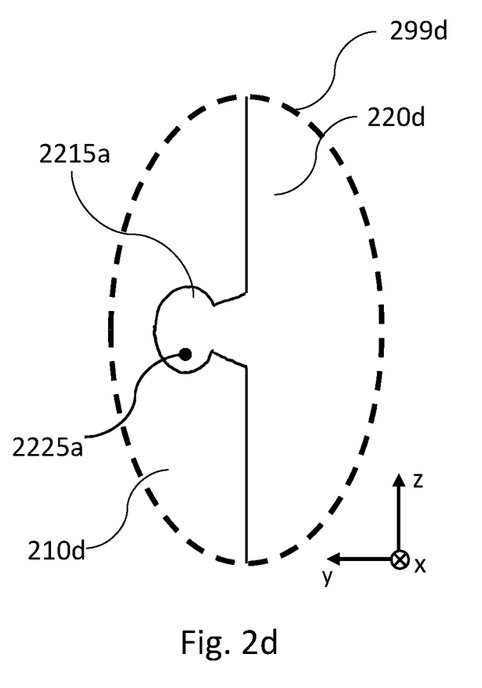

FIG. 2d shows a locking joint 299d including a lollipop-shaped protrusion 2215a of a tail portion 220d received in a corresponding keyhole-shaped recess 2225a of a leaf portion 210d.

Figure 2E:
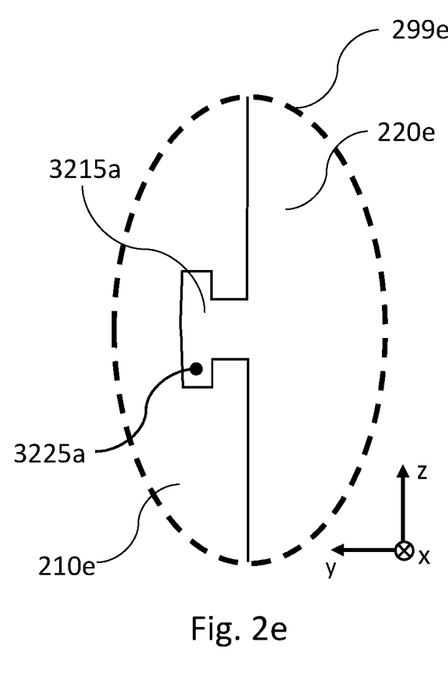

FIG. 2e shows a locking joint 299e including a T-shaped protrusion 3215a of a tail portion 220e received in a corresponding T-shaped recess 3225a of a leaf portion 210e.

Figure 2F:
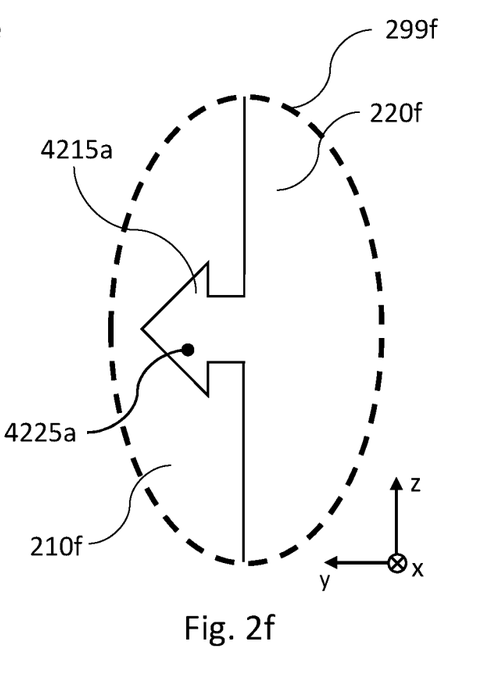

FIG. 2f shows a locking joint 299f including an arrow-shaped protrusion 4215a of a tail portion 220f received in a corresponding arrow-shaped recess 4225a of a leaf portion 210f.

A common feature of the embodiments shown in FIGS. 2c-2f is that there are mating faces (or edges) of the tail portion and leaf portion which provide a stop preventing an external force acting in the longitudinal direction (y) of the leaf from pulling the tail portion and leaf portion apart. That is, the locking joint is arranged such that tension applied between the leaf portion and tail portion in the longitudinal direction (y) of the leaf causes mating faces (or mating edges) of the leaf portion and tail portion to exert a force on each other which is proportional to said tension.

In some embodiments, the locking joint includes a plurality of adjoining pairs of corresponding features in the tail portion and leaf portion. That is, any of the aforementioned functions of the locking joint may be realised by the cooperation of more than one pair of corresponding features in the tail portion and leaf portion. The locking joint may include first and second pairs of corresponding features, wherein the first pair mechanically prevents relative movement of the tail portion and leaf portion in at least a first direction in the plane of the leaf whereas the second pair mechanically prevents relative movement of the tail portion and leaf portion in at least a second direction in the plane of the leaf. The first direction is different from the second direction. The first direction is linear or rotational and the second direction is linear or rotational. For example, the first pair of corresponding features prevents relative linear movement between the tail portion and the leaf portion in the longitudinal direction of the leaf and the second pair prevents relative linear movement between the tail portion and the leaf portion in the transverse direction in the plane of the leaf perpendicular to the longitudinal direction. Together, the first and second pairs prevent relative rotational movement between the tail portion and leaf portion in the plane of the leaf.

In embodiments, the locking joint allows relative movement of the tail portion and leaf portion out of the plane of the leaf (e.g. perpendicular to the plane of the leaf). This allows the leaf portion and tail portion to be overlaid and fastened together in manufacturing by sliding the plane of the tail portion into coplanar alignment with the plane of the leaf portion. For example, the locking joint may be a sliding dovetail joint. Optionally, the locking joint may include an overlapping portion which acts as a stop to prevent further movement of the tail portion in the direction perpendicular to the plane of the leaf as it is brought into coplanar alignment with the leaf portion. For example, the locking joint may be a half blind lap dovetail joint. The overlapping portion increases the strength of the joint under forces acting out of the plane of the leaf.

In embodiments, an adhesive is added between mating surfaces of the locking joint. The overlapping portion of the locking joint described above increases the strength of the locking joint because when adhesive is added to the mating surfaces in the overlapping portion of the locking joint it increases the adhering contact area between the tail portion and the leaf portion. Whether or not an adhesive is used, the overlapping portion increases the strength of the locking joint under torsion and tensile forces.

Lap Joints Between Tail Portion and Leaf Portion

As shown in FIG. 2b, lap joints are formed between the leaf portion 210 and tail portion 220.

The edge of the recess 215 of the leaf portion 210 on the second face is the same as that on the first face except that it further includes a first indent 215a, a second indent 215b and a third indent 215c. The first indent 215a is concave from the central part of the bottom of the U shape of the recess 215. The second indent 215b and third indent 215c are concave from either side of the top of the U shape of the recess 215. The first, second and third indents 215a,b,c are formed through only half of the thickness of the leaf portion 210 and are recessed back from the second face of the leaf portion 210.

The tongue 225 of the tail portion 220 comprises first, second and third protrusions 225a, 225b, 225c corresponding in shape and dimension to first, second and third indents, respectively. The first, second and third protrusions 225a, 225b, 225c are a half thickness of the tail portion 220 and have surfaces which are flush with the second face of the tail portion 220.

The lap joints joining the tail portion 220 and the leaf portion 210 are formed by faces of the leaf portion 210 formed by the first, second and third indents interfacing with faces of the first, second and third protrusions, respectively.

It may be understood that the present disclosure includes lap joints between the tail portion and leaf portion whether or not they are of the locking type described herein. It may also be understood that the present disclosure includes interlocking (or locking) joints between the tail portion and leaf portion whether or not they include an overlap (i.e. as in a lap joint) as described herein.

Leaf Nut and Leaf Nut Holder

FIG. 3a shows a leaf nut 450 located in situ in the first slot section 250a and a leaf actuator screw 430 passing through the leaf nut 450 and located in situ in the first and second slot sections 250a, 250b of the leaf actuator screw slot 250. FIG. 3b is a cross section in a plane parallel to the third plane (xz) and passing through the leaf nut 450, the leaf actuator screw 430 the tail portion 220 in the vicinity of the seat 255.

Leaf Nut

The leaf nut 450 is shown in FIG. 3a, and in cross-section in FIG. 3b. The leaf nut 450 provides a threaded part for the leaf actuator screw 430 to engage therewith in order to convert the rotational motion of the leaf actuator screw about its axis to linear motion in the first and second directions. The leaf nut 450 includes parts 451, 452 which engage with the tail portion 220 in order to resist the rotational force applied to the leaf nut 450 by the rotation of the leaf actuator screw 430. These parts 451, 452 (described in more detail below) allow limited movement of the leaf nut 450 to accommodate misalignment of the leaf drive units 400.

The leaf nut 450 comprises a cylindrical part 457 having a through hole coaxial with the cylindrical part 457. The through hole is dimensioned and threaded to receive the leaf actuator screw 430. The length (i.e. dimension in the first direction when the leaf nut 450 is in situ in the first slot section 250a) of the cylindrical part 457 is approximately equal to two thirds the length (in the first direction) of the first slot section 250a.

The leaf nut 450 also comprises a first block 451 and second block 452 extending outward from opposing portions of the outer cylindrical face of the cylindrical part 457. The first block 451 extends outward from the outer cylindrical face of the cylindrical part 457 in the first direction (when the leaf nut 450 is in situ in the first slot section 250a). The second block 452 extends in the opposite direction to the first block 451 (i.e. in the second direction when the leaf nut 450 is in situ). The length of the first block 451 in the direction of the central axis of the cylindrical part 457 (i.e. the first direction in situ) is equal to the length of the cylindrical part 457 so that the end faces of the cylindrical part 457 are flush with the end faces of the first block 451. The width (i.e. dimension in the fifth direction in situ) of the first block 451 is greater than the internal diameter of the threaded through hole of the leaf nut 450 and less than the outer diameter of the cylindrical part 457.

The first block 451 has a first blind slot 454 formed therein, the first blind slot 454 extending in the second direction from the face of the first block 451 lying parallel to the second plane (xy). The first blind slot 454 runs along the full length of the first block 451 in the first direction. The first blind slot 454 is positioned so that one inner face thereof lies in a plane which lies parallel to the first plane (yz) and passes through the central axis of the cylindrical part 457. In this way, the centre of the first blind slot 454 aligns to one side of the centre of the cylindrical part 457 when viewed in the third plane (xz). This aligns the leaf actuator screw 430 to be more central in relation to the tail portion of the leaf.

The dimensions of the second block 452 and a second blind slot 456 in the second block 452 are the same as those of the first block 451 and first blind slot 454, respectively. The second block 452 and second blind slot 456, respectively, mirror the first block 451 and first blind slot 454 about a plane parallel to the second plane (xy) passing through the central axis of the cylindrical part 457. That is, both the blocks and the blind slots are symmetrical about the plane parallel to the second plane (xy) passing through the central axis of the cylindrical part 457.

The widths first blind slot 454 and second blind slot 456 are dimensioned to receive parts of the tail portion 220 in the seat 255 either side of the first slot section 250a. The parts of the blocks either side of the blind slots straddle the tail portion 220 in the footprint of the seat. This part of the tail portion 220 cooperates with the first block 451 and second block 452 to prevent rotational motion of the leaf nut 450 about the central axis of the cylindrical part 457 when the leaf nut 450 is in situ. Thus, the torque of the leaf actuator screw 430 applied to the leaf nut 450 when the leaf actuator screw 430 is rotated about its axis does not translate into rotation of the leaf nut 450.

The depths (i.e. dimensions in the first direction) of the first blind slot 454 and second blind slot 456 are such that leaf nut 450 can travel a limited (but non-zero) distance in the first and second directions in the first slot section 250a. The movement of the leaf nut 450 in these directions accommodates small misalignments of the leaf actuator screw 430, for example due to misalignments of the leaf actuator motors in the mounting plate 510, or misalignment of the mounting plate 510 relative to the leaf bank 20.

Leaf Nut Holder

Figure 4B:
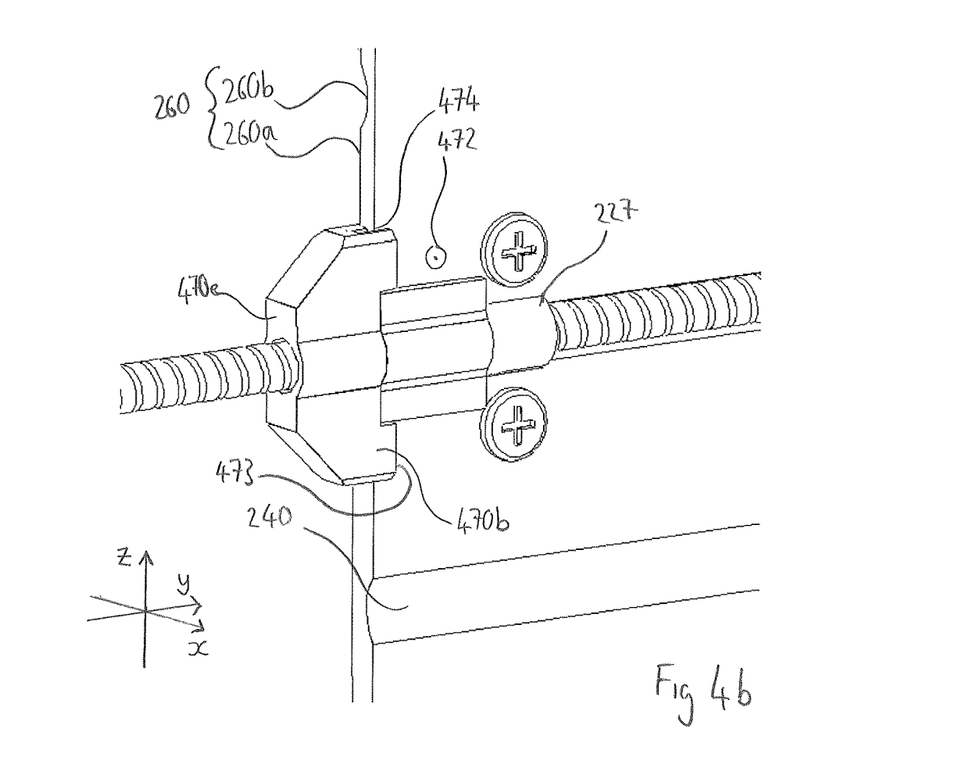
FIG. 4b shows an isometric view of a face of the tail portion in the vicinity of a seat in the tail portion.

FIGS. 4a and 4b show a leaf nut holder 470 arranged to hold the leaf nut 450 in position in the tail portion 220 of the leaf 200. FIG. 4a shows an isometric view of the second face of the tail portion 220 in the vicinity of the seat 255. FIG. 4b shows an isometric view of the first face of the tail portion 220 in the vicinity of the seat 255.

The leaf nut holder 470 is structure for housing the leaf nut 450. The leaf nut holder can be coupled to the leaf 200. The leaf nut holder 470 prevents linear movement of the leaf nut 450 in the direction of the axis of the leaf actuator screw 430. The leaf nut holder 470 allows limited (non-zero) movement of the leaf nut 450 in the plane of the leaf 200.

Notwithstanding the features described below, the leaf nut holder 470 is a substantially oblong block having a length (i.e. dimension in the first direction when in situ in the tail portion 220) approximately 50% larger than the length of the seat 255 and a width (i.e. dimension in the third direction when in situ) substantially equal to the width of the seat 255. When in situ on the tail portion 220 of the leaf 200, the leaf nut holder 470 has a first face 470a and a second face 470b each substantially parallel to the first plane (yz), a third face 470c and fourth face 470d each parallel to the second plane (xy) and a fifth face 470e and sixth face 470f each parallel to the third plane (xz). The cross-sectional profile of the leaf nut holder 470 in the third plane (xz) is such that the first face 470a of the leaf nut holder 470 has a surface topography which is the inverse of that of the composite groove 260 in the second face of the tail portion 220. Notwithstanding the features described below, the second face 470b of the leaf nut holder 470 has a surface topography which is the mirror image of the first face 470a about a plane parallel to the first plane (yz) passing through the centre of the leaf nut holder 470.

A nut guide 475 arranged to receive the leaf nut 450 is formed through the leaf nut holder 470. The nut guide 475 is an aperture passing approximately centrally through the leaf nut holder 470 in the fifth direction. The length of the nut guide 475 (in the first direction) is substantially the same as the length of the leaf nut 450. Thus, movement of the leaf nut 450 is restricted by the leaf nut holder 470 in the first and second directions. The width of the nut guide 475 (in the third direction) is marginally greater than the width of the leaf nut 450 so that movement of the leaf nut 450 is permitted inside the nut guide 475 in the third and fourth directions. The range of movement of the leaf nut 450 allowed by the cooperation of the first blind slot 454 and second blind slot 456 in the leaf nut 450 with the first slot section 250a in the tail portion 220 is substantially equal to the range of movement of the leaf nut 450 allowed by the width of the nut guide 475.

The leaf nut holder 470 has a cutaway portion 472 to receive the second face of the tail portion 220 of the composite leaf 200. The cutaway portion 472 is recessed back into the leaf nut holder 470 in the sixth direction from the second face 470b of the leaf nut holder 470. A void formed by the cutaway portion 472 extends over the full width and over more than half of the length of the leaf nut holder 470 so that the cutaway portion 472 defines a single shoulder 473 running in the first direction and having a face parallel to the third plane (xz). A locating slot 474 is formed in the face of the shoulder to receive the third edge 223 of the tail portion 220.

The leaf nut holder 470 has two threaded through holes extending in the third direction. The axes of the threaded through holes are collinear with the respective axes of the two through holes in the seat 255 when the leaf nut holder 470 is in situ on the tail portion 220. The leaf nut holder 470 is fixed to the tail portion 220 by screws inserted through the respective through holes in the seat 255 and into the threaded through holes in the leaf nut holder 470. A ridge formed by the shoulder 473 and locating slot 474 formed therein provides further rigidity by applying a resistive force to third edge 223 of the tail portion 220 to prevent the end of the leaf nut holder 470 farthest from the leaf portion 210 from moving in the sixth direction. The locating slot provides a resistive force which prevents the leaf nut holder 470 from moving in the first direction. Thus, the third edge 223 of the tail portion 220 forming an edge of the seat 255 is received in the slot so that the leaf nut holder 470 straddles this part of the tail portion 220.

The fifth face 470e of the leaf nut holder 470 is that parallel to the third plane and distal from the leaf portion 210 when in situ. A screw guide hole 478 is formed in the leaf nut holder 470 which extends from the centre of the fifth face 470e and in the first direction through the volume of the leaf nut holder 470. The screw guide hole 478 receives the leaf actuator screw 430 and provides clearances in the third, fourth, fifth and sixth directions which allow movement of the leaf actuator screw 430 inside the leaf nut holder 470 in these directions. Thus, the leaf nut holder 470 is arranged to allow movement of the leaf nut 450 and the leaf actuator screw 430 relative to the leaf nut holder 470 (and thus relative to the tail portion 220 of the composite leaf) in the third and fourth directions.

The leaf nut holder 470 includes 45-degree chamfers between the third face 470c and the fifth face 470e, and between the fourth face 470d and the fifth face 470e so that the dimension of the fifth face 470e in the third direction is around a half that of the leaf nut holder 470.

Chamfers are also formed between the third face 470c and each of the first and second face 470b and between the fourth face 470d and each of the first face 470a and second face 470b of the leaf nut holder 470. These chamfers enable smoother movement of the leaf nut holder 270 of one leaf in the composite or first groove of an adjacent leaf.

Where the terms attenuation factor, attenuation factor per unit width, attenuation factor per unit length and attenuation factor per unit area are used, it may be understood that these parameters are measured (or calculated) in the radiation energy range 6 MeV to 25 MeV, or a subrange therein, e.g. 6 MeV to 10 MeV.

It may be understood that when the terms 'parallel', 'perpendicular' or 'in the plane of' are used to describe the relative arrangement of features and components, small deviations therefrom are permitted provided that they do not affect the functional and/or operational aspects of the multi-leaf collimator modules described herein.

Features of the above aspects can be combined in any suitable manner. It will be understood that the above description is of specific embodiments by way of aspect only and that many modifications and alterations will be within the skilled person's reach and are intended to be covered by the scope of the appendant claims.

Also described herein are the following numbered clauses:

E1. A leaf for a multi-leaf collimator, the leaf comprising a tail portion adjoined to a leaf portion by a locking joint.

E2. The leaf according to clause E1, wherein the locking joint mechanically prevents separation of the tail portion and the leaf portion by a first force acting in the plane of the leaf.

E3. The leaf according to clause E2, wherein the first force acts in a longitudinal direction of the leaf.

E4. The leaf according to clause E3, wherein the longitudinal direction extends from an edge of the tail portion to an edge of the leaf portion.

E5. The leaf according to any of clauses E1-E4, wherein the locking joint is a dovetail joint.

E6. The leaf according to clause E5, wherein the dovetail joint is a sliding dovetail joint or a half-blind dovetail joint.

E7. The leaf according to any of clauses E1-E6, wherein the locking joint mechanically allows separation of the tail portion and leaf portion by a force acting perpendicular to the plane of the leaf.

E8. The leaf according to any of clauses E1-E7, wherein one of the tail portion and leaf portion comprises a protrusion, the other of the tail portion and leaf portion comprises a corresponding recess and the protrusion and recess interlock to form the locking joint.

E9. The leaf according to any of clauses E1-E8, wherein the tail portion comprises a first material and the leaf portion comprises a second material which is different from the first material.

E10. The leaf according to any of clauses E1-E9, wherein the locking joint mechanically prevents any linear or rotational movement of the leaf portion and tail portion relative to each other in the plane of the leaf.

The invention claimed is:

1. A leaf for a multi-leaf collimator, the leaf comprising: a tail portion adjoined to a leaf portion by a locking joint.

2. The leaf according to claim 1, wherein the locking joint mechanically prevents separation of the tail portion and the leaf portion by a first force acting in a plane of the leaf.

3. The leaf according to claim 2, wherein the first force acts in a longitudinal direction of the leaf.

4. The leaf according to claim 3, wherein the longitudinal direction extends from an edge of the tail portion to an edge of the leaf portion.

5. The leaf according to claim 1, wherein the locking joint is a dovetail joint.

6. The leaf according to claim 5, wherein the dovetail joint is a sliding dovetail joint or a half-blind dovetail joint.

7. The leaf according to claim 1, wherein the locking joint mechanically allows separation of the tail portion and leaf portion by a force acting perpendicular to a plane of the leaf.

8. The leaf according to claim 1, wherein one of the tail portion or the leaf portion comprises a protrusion, the other of the tail portion or the leaf portion comprises a corresponding recess, and wherein the protrusion and the corresponding recess interlock to form the locking joint.

9. The leaf according to claim 1, wherein the tail portion comprises a first material and the leaf portion comprises a second material which is different from the first material.

10. The leaf according to claim 1, wherein the locking joint mechanically prevents any linear or rotational movement of the leaf portion and tail portion relative to each other in a plane of the leaf.

* * * * *